(12) United States Patent
Gurtner (10) Patent No.: US 7,407,492 B2
(45) Date of Patent: Aug. 5, 2008

(54) READING AID FOR A DEVICE FOR ADMINISTERING A SETTABLE DOSAGE OF AN INJECTABLE PRODUCT

(75) Inventor: Thomas Gurtner, Koppigen (CH)

(73) Assignee: TecPharma Licensing, AG, Burgdorf (CH)

( * ) Notice: Subject to any disclaimer, the term of this patent is extended or adjusted under 35 U.S.C. 154(b) by 342 days.

(21) Appl. No.: 10/638,828

(22) Filed: Aug. 11, 2003

(65) Prior Publication Data

US 2004/0030293 A1 Feb. 12, 2004

Related U.S. Application Data

(63) Continuation of application No. PCT/CH02/00060, filed on Feb. 4, 2002.

(30) Foreign Application Priority Data

Feb. 12, 2001 (DE) ................. 101 06 367

(51) Int. Cl.
*A61M 5/00* (2006.01)
(52) U.S. Cl. .............. 604/181; 604/135; 604/136; 604/137
(58) Field of Classification Search .......... 604/71, 604/181, 187, 208, 211, 209, 210, 246, 248, 604/189, 220, 68, 118, 186, 207
See application file for complete search history.

(56) References Cited

U.S. PATENT DOCUMENTS

| | | | | |
|---|---|---|---|---|
| 5,112,317 | A * | 5/1992 | Michel | 604/208 |
| 5,114,406 | A * | 5/1992 | Gabriel et al. | 604/136 |
| 5,498,243 | A * | 3/1996 | Vallelunga et al. | 604/197 |
| 5,637,094 | A * | 6/1997 | Stewart et al. | 604/135 |
| 6,001,089 | A | 12/1999 | Burroughs et al. | |
| 6,106,501 | A | 8/2000 | Michel | |
| 6,210,369 | B1 | 4/2001 | Wilmot et al. | |
| 6,221,046 | B1 * | 4/2001 | Burroughs et al. | 604/153 |
| 6,235,004 | B1 * | 5/2001 | Steenfeldt-Jensen et al. | 604/207 |

(Continued)

FOREIGN PATENT DOCUMENTS

EP 0937477 A2 8/1999

(Continued)

*Primary Examiner*—Kevin C. Sirmons
*Assistant Examiner*—Phillip Gray
(74) *Attorney, Agent, or Firm*—David E. Bruhn, Esq.; Dorsey & Whitney LLP (57) ABSTRACT

A plug-on body which can be plugged onto a device for administering a settable dosage of an injectable product, the plug-on body including a first plug-on body section extending axially in the direction of a plug-on body axis for fixing the plug-on body to a dosing and activating means, a shifting stopper formed by the first plug-on body section and operating by positive lock for axially fixing the plug-on body with respect to at least one shifting direction, a rotational stopper formed by the first plug-on body section and operating by positive lock for fixing the plug-on body against rotating, a second plug-on body section extending behind the first plug-on body section in the direction of the plug-on body axis, wherein said second plug-on body section forms an optics system for reading a dosage scale on a dosing element of the device which serves to set the dosage.

16 Claims, 8 Drawing Sheets

U.S. PATENT DOCUMENTS

| | | | |
|---|---|---|---|
| 6,514,230 B1 * | 2/2003 | Munk et al. | 604/207 |
| 6,666,849 B1 * | 12/2003 | Marshall et al. | 604/246 |
| 6,699,224 B2 * | 3/2004 | Kirchhofer et al. | 604/208 |
| 6,770,056 B2 * | 8/2004 | Price et al. | 604/246 |
| 2005/0101917 A1 * | 5/2005 | Doyle | 604/187 |

FOREIGN PATENT DOCUMENTS

| | | |
|---|---|---|
| WO | WO 99/64092 | 12/1999 |

\* cited by examiner

READING AID FOR A DEVICE FOR ADMINISTERING A SETTABLE DOSAGE OF AN INJECTABLE PRODUCT

CROSS-REFERENCE TO RELATED APPLICATION

This application is a continuation of International Application No. PCT/CH02/00060, filed on Feb. 4, 2002, which claims priority to earlier filed German Application 101 06 367.9, filed on Feb. 12, 2001.

BACKGROUND

The present invention relates to administering injectable products. More particularly, it relates to devices and methods for administering injectable products by means of a device on which a product dosage to be administered can be set. The product is typically a fluid that is medically and/or cosmetically effective. Insulin and growth hormones may be cited by way of example.

In general, there is a requirement not only that different product doses can be administered using the same device, but also that the product dosages can be set finely graded. In particular, in human medical applications, though in principle also in veterinary applications, the precision in setting the product dosage must be ensured with as great a reliability as possible. A particular problem with regard to administering reliability is raised by self-administering, in which a person administers a product to himself/herself. Unintentionally or even unnoticeably adjusting an already set product dosage can have serious negative consequences. Failing to accurately and clearly read the set dosage on the dosage scale of the device can also create problems.

SUMMARY

It is therefore an object of the invention to increase the reliability in administering a settable dosage of an injectable product using simple means, such that the desired product dosage is indeed administered.

In one embodiment, the present invention comprises a plug-on body which can be coupled to an injection device for administering a settable dosage of an injectable product, the plug-on body comprising a first body section comprising a shifting stopper and a rotational stopper, and a second body section comprising an optics system for reading a dosage scale associated with the injection device.

In one embodiment, the present invention comprises a plug-on body which can be plugged onto a device for administering a settable dosage of an injectable product, the plug-on body including a first plug-on body section, extending axially in the direction of a plug-on body axis, for fixing the plug-on body to a dosing and activating means, a shifting stopper formed by said first plug-on body section and operating by positive lock for axially fixing the plug-on body with respect to at least one shifting direction and a rotational stopper formed by the first plug-on body section and operating by positive lock for fixing the plug-on body against rotating, and a second plug-on body section, extending behind the first plug-on body section in the direction of said plug-on body axis, wherein said second plug-on body section forms an optics system for reading a dosage scale on a dosing element of the device which serves to set the dosage.

The present invention relates to devices for administering a settable dosage of an injectable product. Typically, such devices comprise a casing, a reservoir for the product formed or accommodated by the casing, a delivering means for delivering the product dosage to be administered, i.e., the set product dosage, from the reservoir and a dosing and activating means connected to the casing.

The dosing and activating means fulfils the functions of setting the dosage and activating the delivering means. It is therefore connected to the casing in such a way that can perform a dosing movement relative to the casing on the one hand and a delivering movement on the other. The product dosage is set by the dosing movement. The delivering means is activated by the delivering movement of the dosing and activating means. In preferred embodiments, the dosing and activating means comprises a dosing element for fulfilling the function of setting the dosage and an activating element for fulfilling the function of activating the delivering means. It should also not be ruled out that both functions and movements are performed by means of a single dosing and activating element. The dosing movement and/or delivering movement can also be just the movement of a switch or a key. The dosing movement is preferably a rotational movement and the delivering movement is preferably a translational movement, although the forms of movement can also be assigned the other way around. The dosing movement and delivering movement can be a unitary movement, for example, a translational movement. In some preferred embodiments, a translational movement occurs along a rotational axis of a rotational dosing movement.

The delivering means can in principle be realized by any suitable form of pump. In some preferred embodiments, the delivering means comprises a piston which is accommodated in the reservoir and can be shifted towards a reservoir outlet, and which advances to deliver and administer the set product dosage through the outlet. In a preferred embodiment with a piston pump, the delivering means comprises a piston rod acting on the piston in the direction of the reservoir outlet. The dosing movement of the dosing and activating means reduces a gap between the piston and the piston rod. By then linearly shifting the piston rod, the piston is advanced towards the reservoir outlet and the product dosage set by adjusting the gap is delivered. The piston rod can be formed as a threaded rod which, together with a drive member provided with a counter thread, forms a spindle drive. The dosing movement of the dosing and activating means rotates the drive member relative to the casing. Via the spindle drive, and by linearly guiding the piston rod, the piston rod is moved towards the piston and the product dosage is thus set. Instead of setting the product dosage by means of a spindle drive, it can also for example be set via a gear rack. When setting the product dosage by means of a gear rack drive, this is also preferably by way of a rotational movement of the dosing movement of the dosing and activating means. Examples of two ways of setting the dosage are known from DE 197 17 107 and WO 97/36626, which are referenced by way of example with respect to their functionality and do not rule out other arrangements for setting the dosage and delivering the product.

The product can be administered via an infusing part, in particular an injection needle, or also without an infusing part in the form of a penetrating pressurized jet.

In a device of the type described above, as set forth in the invention, a reading aid is formed by a plug-on body by providing the plug-on body with an optics system which makes it easier to read a dosage scale. The plug-on body is formed such that, when the plug-on body is connected to the casing of the device, the optics system is situated radially above the dosage scale and magnifies it for the observer. In one preferred exemplary embodiment, the optics system is formed as a simple reading-glass or magnifying lens. In an equally preferred embodiment, the optics system can also comprise a number of lenses, using which the part of the dosage scale beneath a first lens, for example a marking bar and/or a measuring symbol or measuring number, is magnified and transmitted to a display, as appropriate by deflecting the corresponding light beam. Such an optics system can also comprise a light conductor. By transmitting it onto a display attached to the plug-on body, the product dosage set can be displayed particularly conveniently, and as appropriate magnified a number of times through a number of lenses.

The plug-on body can form not only a reading aid, but also an adjustment block, in that the blocking body, when connected to the casing, prevents the dosing movement of the dosing and activating means. When connected, the plug-on body shields the dosing and activating means such that access to a dosing element of the dosing and activating means, which could effect an adjustment, is no longer possible. Instead of or in addition to shielding against access, the plug-on body can be in a locking engagement with the casing, said locking engagement preferably being based only on a positive lock. As used herein, the term "block" is intended to include shielding alone, locking alone, a combination of shielding and locking, and/or other suitable functions.

Once the connection has been established, the plug-on body can be connected to the casing, non-detachably or, in some preferred embodiments, detachably. If the plug-on body forms not only the reading aid but additionally also the adjustment block, then the connection allows the blocking body to be moved at least once from a starting position in which a dosing movement is possible into a shielding and/or locking position in which it is no longer possible.

In some preferred embodiments, a plug-on body for forming the reading aid is a separate, preferably one-piece part. In the embodiment as a combined reading aid and adjustment block, the plug-on body is connected to the casing such that it enters into an engagement which locks the dosing movement and/or shields the dosing and activating means such that access for performing the dosing movement is no longer possible. The plug-on body is formed such that, when connected, it can no longer be moved relative to the casing. If a locking engagement, locking the dosing movement, is formed between the plug-on body and the dosing and activating means, the blocking body is sufficiently rigid, due to being itself fixed to the casing and the locking engagement, to fix the dosing and activating means relative to the casing with respect to its dosing movement. If the blocking effect of the plug-on body is based on the fact that the dosing and activating means is shielded by the plug-on body such that access required for performing the dosing movement is prevented, then it is in principle sufficient if connecting the plug-on body to the casing ensures that the plug-on body can at least not be unintentionally moved out of its shielding position. In some preferred embodiments, the plug-on body is a rigid body. As a reading aid alone, the plug-on body may also preferably be a rigid body.

The additional function of an adjustment block is particularly advantageous in cases in which the dosage to be administered is pre-set by a doctor and the pre-set dosage is repeatedly administered by a user. In principle, the dosage can of course also be pre-set by the person wishing to administer the product dosage to himself/herself. Administering an incorrect dosage, for example by unnoticeably adjusting the dosage, is practically ruled out.

The plug-on body is designed such that it can be connected to the casing by means of a plug connection which is sufficiently stable for its magnifying effect, and preferably for a blocking effect. The plug-on body is shaped such that, once the plug connection has been established, the optics system comes to rest above the dosage scale. In some embodiments, the plug connection is preferably defined in such a way that the plug-on body always assumes the same position relative to the casing, even when the plug-on body is repeatedly attached to the casing of the device. In some embodiments, the plug-on body is preferably formed as a shell body and particularly as a sleeve body, which is slid over the casing and in particular a dosing element of the dosing and activating means. In some embodiments, a defined position of the plug-on body relative to the casing is preferably established by one or more positively acting engaging means on the plug-on body and on the casing. It is advantageous if a latching connection is formed between the casing and the plug-on body. The latching connection can even form the plug connection between the plug-on body and the casing by itself. The latching connection can also ensure that the plug-on body is held in positive engagement with the casing, such that the latching connection firstly has to be released in order to release the positive engagement and thus be able to remove the plug-on body from the casing.

As compared to an integrated reading aid on the device, forming the reading aid by means of a separate plug-on body has the advantage that no costly modifications have to be made to devices which do not inherently comprise a reading aid, on which the dosage scale set can therefore be read. This can in particular be advantageous when devices which have hitherto been produced without a reading aid are to be fitted with a reading aid. Modifications in production due to one or more engaging means which possibly have to be provided on the casing can be made at comparatively little cost. It is perfectly possible to form the plug-on body such that recesses, indentations or protrusions and the like, already provided on the respective casing, can be used for a positive engagement with the casing, and one or more corresponding engaging elements can be formed on the plug-on body.

If the dosing element of the dosing and activating means is provided with the dosage scale, as is in general usual, then the plug-on body forming the reading aid is fixedly connected to the casing, such that the reading-glass comes to rest above the dosage scale of the dosing element. If the casing is provided with the dosage scale, the plug-on body is fastened to the dosing element performing the dosing movement, such that the reading-glass participates in the dosing movement and is thus moved over the dosage scale.

BRIEF DESCRIPTION OF THE DRAWINGS

The invention will now be explained by way of exemplary preferred embodiments.

DETAILED DESCRIPTION

Figure 1:
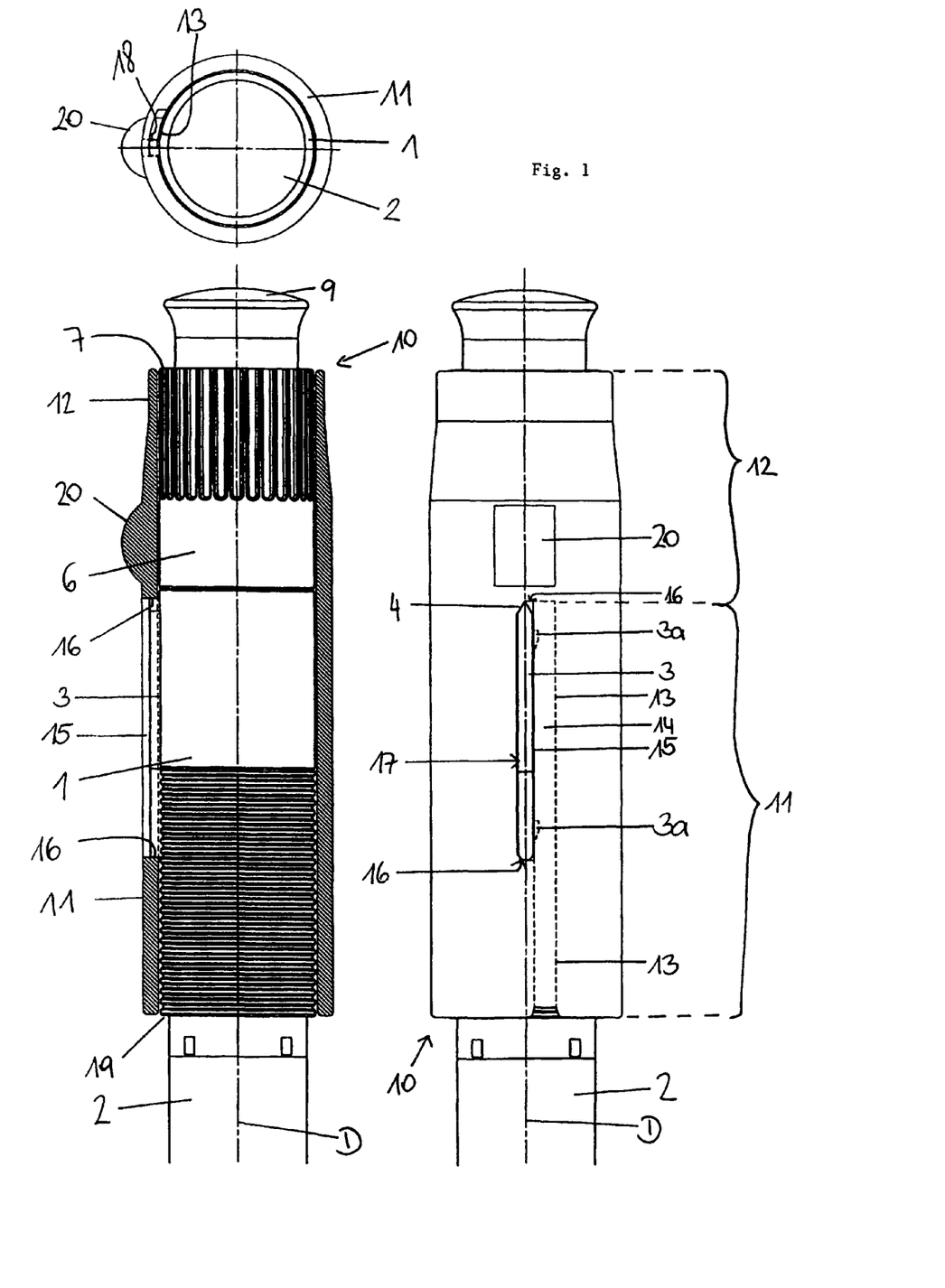
FIG. 1 depicts an adjustment block, formed by a plug-on body fastened to an injection apparatus, as set forth in a first exemplary embodiment.
Figure 2:
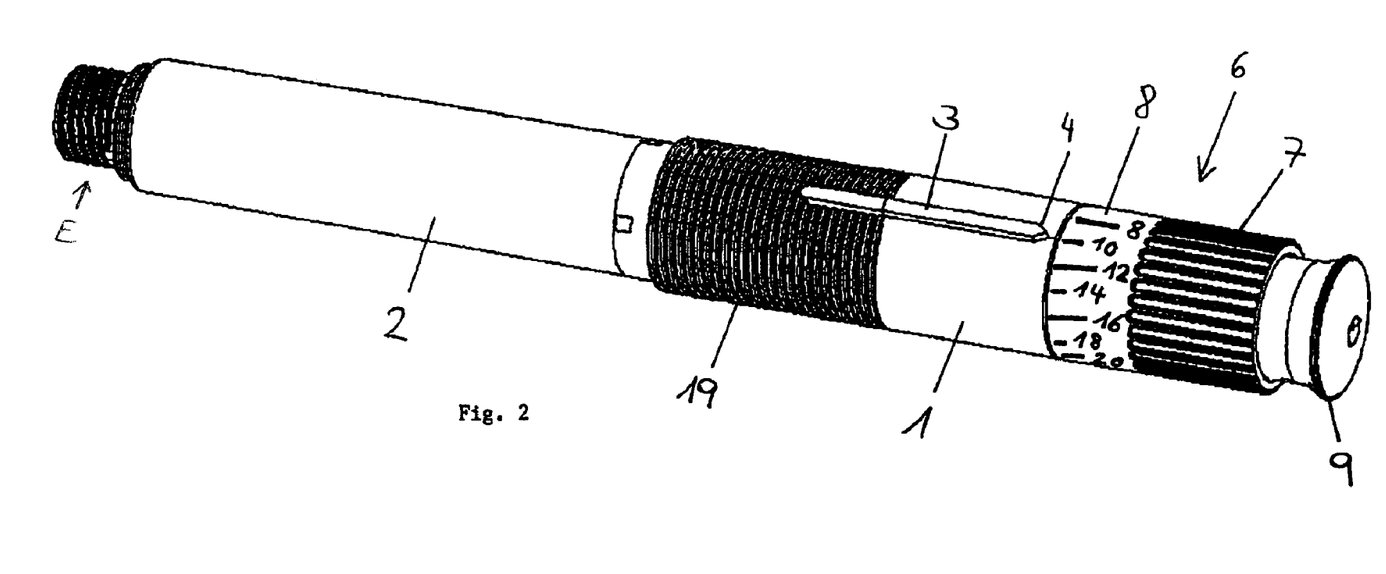
FIG. 2 depicts the injection apparatus of FIG. 1.
Figures 3, 5:
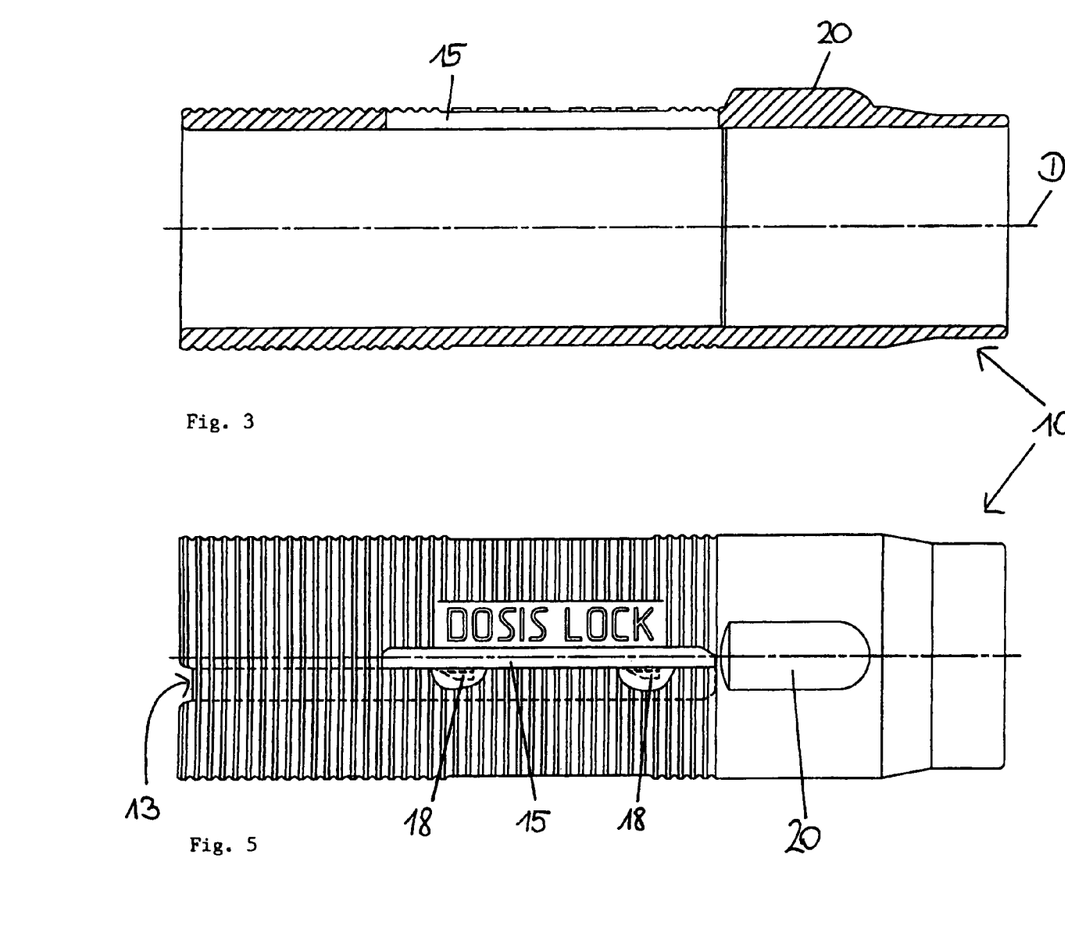
FIG. 3 depicts the plug-on body of FIG. 1, in a longitudinal section.
FIG. 5 depicts the plug-on body in a view.
Figure 4:
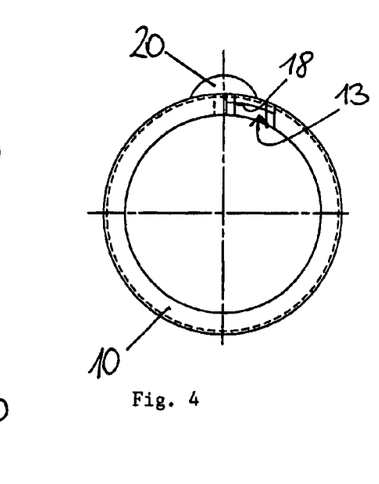
FIG. 4 depicts the plug-on body in a cross-section.

FIG. 1 shows a view, a longitudinal section and a top view of a combined reading aid and adjustment block, which is formed on an injection apparatus comprising a plug-on body 10. Only a rear part of the injection apparatus, which in the exemplary embodiment is a so-called injection pen, is illustrated, the plug-on body 10 having been slid over or plugged onto said rear part. The injection apparatus is shown in FIG. 2, except for its foremost part, without the plug-on body 10. FIGS. 3 to 5 show a plug-on body 10 which deviates from the plug-on body 10 of FIG. 1. The plug-on body 10 of FIG. 1 can be directly replaced by the plug-on body 10 of FIGS. 3 to 5. The first exemplary embodiment is therefore described in an overview of FIGS. 1 to 5.

The injection apparatus (FIG. 2) comprises an ampoule holder 2 and a guiding part 1 connected to the ampoule holder 2, secured against rotating and shifting. The holder 2 and guiding part 1 may be regarded as forming the casing of the injection apparatus. The ampoule holder 2 serves to accommodate an ampoule filled with a product to be administered, for example insulin. A dosing and activating means forms the rearmost part of the injection apparatus and is supported by the guiding part 1 such that it can perform a dosing movement for setting a product dosage to be administered and a delivering movement for activating a delivering means. The dosing and activating means comprises a dosing element 6 and an activating element 9. The sleeve-shaped dosing element 6 can be rotated about its central longitudinal axis, relative to the guiding part 1. The dosing movement is a rotational movement of the dosing element 6 about the rotational axis D formed by the central longitudinal axis. The activating element 9 can be shifted back and forth along the rotational axis D of the dosing element 6, relative to the guiding part 1 and relative to the dosing element 6. By shifting the activating element 9 backwards, the ampoule can be raised, i.e., filled with new product. Shifting the activating element 9 towards the front end of the injection apparatus activates the delivering means. To set the product dosage, the dosing element 6 acts, via a spindle drive or a gear rack drive, such as are presumed to be known in principle, on a piston rod which is shifted along the rotational axis D, relative to the guiding part 1 and the ampoule holder 2, by the dosing movement of the dosing element 6. In particular, the dosing movement linearly shifts the piston rod and reduces a slight gap between a piston accommodated in the ampoule and a front active end of the piston rod, setting a product dosage which may be delivered from dose delivery end E by a subsequent delivering movement of the activating element 9.

The dosing element is provided with a grip aid 7 which is formed as a ribbing comprising linear ribs extending in the direction of the rotational axis D. On the dosing element 6, a dosage scale 8 is printed on the circumference of an end facing the guiding part 1, said dosage scale 8 in combination with a marking arrow 4 enabling the product dosage set to be read. The marking arrow 4 is arranged opposite the dosage scale on a rear end of the guiding part 1 and is fixedly connected to the guiding part 1. The marking arrow 4 forms a rear end of a protrusion 3 which radially projects from an outer surface area of the guiding part 1. In the exemplary embodiment, the protrusion 3 including its rear end forming the marking arrow 4 is formed as a linear rib extending in the direction of the rotational axis D of the dosing element 6.

The protrusion 3 forms an engaging means of the casing for fixing the plug-on body 10. FIG. 1 shows the injection apparatus and the plug-on body 10 after a connection has been established in which the plug-on body 10 is connected axially, i.e., in the direction of the rotational axis D of the dosing element 6, to the guiding part 1, and secured against rotating with respect to said rotational axis D.

In the exemplary embodiment, the plug-on body 10 is formed by a sleeve body which is shaped in strict adjustment with the outer shape of the injection apparatus, in particular the guiding part 1. As a whole, the sleeve body forms a hollow cylinder. The plug-on body 10 comprises a first plug-on body section 11 and a second plug-on body section 12 in a row in the longitudinal direction. The first plug-on body section 11 fulfils the function of fastening to the casing. The second plug-on body section 12 fulfils the function of shielding the dosing element 6 against access, through which a dosing movement of the dosing element 6 could be performed, and the dosing element 6 thus adjusted. In the exemplary embodiment, the second plug-on body section 12 is a continuous sleeve part and surrounds the dosing element 6 along its entire length. The second plug-on body section 12 need not necessarily be formed as a closed sleeve, but may indeed comprise breaches, although the dosing element 6 must be secured against unintentional access by being inadvertently handled, for example by children, if the blocking effect of the plug-on body 10 is based solely on shielding the dosing element 6, as in the exemplary embodiment. In addition to shielding, the plug-on body 10 can also be formed for a locking engagement with the dosing element 6.

The first plug-on body section 11 forms two shifting stoppers 16, which operate by positive lock and prevent the plug-on body 10 from moving along the rotational axis D of the dosing element 6 in either direction. It furthermore forms a rotational stopper 17 which operates by positive lock and prevents the plug-on body 10 from rotating about the rotational axis of the dosing element 6 with respect to a rotational direction. Relative rotation in the opposite direction with respect to the casing is prevented by means of a detachable latching connection.

For forming the cited stoppers 16 and 17 and the latching connection, the plug-on body 10 is provided in the first plug-on body section 11 with a recess 13 on an inner surface area. The recess 13 is a blind recess. The recess 13 extends from a front facing side of the plug-on body 10 in the direction of the longitudinal axis of the plug-on body 10. When it is connected to the casing, the longitudinal axis of the plug-on body 10 is parallel to the rotational axis D of the dosing element 6; in one preferred embodiment, it corresponds to the rotational axis D of the dosing element, as in the exemplary embodiment. Viewed in the circumferential direction of the plug-on body 10, the recess 13 is sufficiently wide over its entire length to be able to accommodate the protrusion 3 formed on the guiding part 1. Viewed in the circumferential direction, the recess is widened in a rear area which forms a rear end of the recess 13. The widening 15 of the recess 13 thus formed comprises radial limiting walls which form the shifting stoppers 16 and the rotational stopper 17 of the plug-on body 10. The limiting wall forming the rotational stopper 17 extends in the longitudinal direction of the plug-on body 10. The limiting walls facing opposite each other and forming the shifting stoppers 16 extend in the circumferential direction of the plug-on body 10. When it is connected, the protrusion 3 of the casing in the widening 15 is simultaneously pressed onto the rotational stopper 17 and the shifting stoppers 16.

In order to prevent a reverse rotational movement which is not locked by the stoppers 16 and 17 on the plug-on body side, the plug-on body 10 is provided with at least one latching element, in the exemplary embodiment two latching elements 18 (FIG. 5). The latching elements 18 cooperate in pairs with latching elements 3a formed on the casing by forming a detachable latching connection with the latching means 3a.

A reading-glass 20 is formed in the area of the second plug-on body section 12. The reading-glass 20 is arranged directly behind the widening 15, viewed in the direction of the longitudinal axis of the plug-on body 10, such that once the plug-on body 10 has been fixed to the casing, the reading-glass 20 is above the dosing scale 8 of the dosing element 6 and the dosage scale 8 can be read through the reading-glass 20. Optical magnification by the reading-glass 20 makes it easier to read the dosage scale 8 and thus also makes setting the product dosage more reliable. Once the plug-on body 10 has been fixed, the tip of the marking arrow 4 points to the center of the reading-glass 20.

The part of the recess 13 forming the blind groove which extends as far as the front facing area of the plug-on body 10 is not shaped as an breach but rather only as a cavity 14 in the first plug-on body section 11. The widening 15 forming the shifting stopper 16 and the rotational stopper 17 of the plug-on body 10 breaches the second plug-on body section 12 over its entire area, such that when connected, the marking arrow 4 is clearly visible. The part of the recess 13 formed only as a cavity 14 can in principle also be formed as a breach. It would be equally conceivable to form the widening 15 merely as a cavity. In addition to being easier to read, however, forming it as a breach also has manufacturing advantages, when the plug-on body 10 is preferably manufactured as a plastic injection-molded part.

The plug-on body 10 can be manufactured, in its entirety or to a large extent, from a transparent material and formed such that the magnified dosage scale 8 of the dosing element 6 is inherently readable, without forming the reading-glass as a separate area. If the plug-on body 10 consists of an opaque material, though also in principle also in the case of a transparent material, the reading-glass 20 can be inserted into a viewing window, or for example when manufacturing the plug-on body 10 as an injection-molded part can be trans-fused with the plug-on body material in the injection mold.

In the exemplary embodiment, a ribbing 19 for increasing the grip of the injection apparatus is provided in a front area of the guiding part 1. Instead or in addition, a ribbing which likewise increases the grip can be formed on the outer side of the plug-on body section 11. FIGS. 3 to 5 show such a plug-on body 10 by way of example. As can also be seen in FIGS. 5 and 6, each of the latching means 18 is formed by a latching projection on a surface area of the plug-on body 10. In the exemplary embodiment, the latching elements 18 are latching projections which project radially inwards. The latching means 3a of the casing are also formed by latching projections which slide over the latching projections 18 and snap in behind the latching elements 18 in order to establish the latching connection. The latching elements 18 or the latching elements 3a could also be shaped as pockets into which the latching projections snap. The latching connection can also be formed by just one or by more than two latching elements on each of the plug-on body 10 and the casing.

Mounting the plug-on body 10 of the first exemplary embodiment on the casing of the injection apparatus is very easily possible via the dosing and activating means, comprising dosing element 6 and activating element 9. Once the desired product dosage has been set by rotating the dosing element 6, the plug-on body 10 is slid over the activating element 9 and the dosing element 6 onto the casing from the rear. Because of the small radial gap from the dosing element 6 and the casing, the recess 13 has to be brought flush with the protrusion 3 in order to slid the plug-on body 10 on, such that alone through the protrusion 3 engaging with the recess 13, the plug-on body 10 is linearly guided in the direction of the rotational axis D of the dosing element 6 as it is slid on. The plug-on body 10 is slid on until the reverse end of the protrusion 3, formed in the exemplary embodiment by the marking arrow 4, comes to rest against the rear shifting stopper 16 of the plug-on body 10. The sliding-on process is then complete. In this shifting position, the plug-on body 10 and the injection apparatus are rotated about the rotational axis D relative to each other, such that the protrusion 3 comes to rest against the rotational stopper 17. Due to the specific shape of the protrusion 3 as a linear rib and of the widening 15 as a linear recess adjusted in its shape to the protrusion 3, the protrusion 3 is accommodated in the widening 15 such that it also has contact with the front shifting stopper 16. At the same time as the stopper position is reached with respect to the rotational movement, the latching elements 3a of the injection apparatus and the latching elements 18 of the plug-on body 10 latch with each other. In this moment, the plug-on body 10 is fixed to the injection apparatus such that it cannot be shifted or rotated, wherein the fixture via the shifting stoppers 16 and the fixture via the rotational stopper 17 is absolutely fixed and the fixture via the latching connection is releasable.

Figure 6:
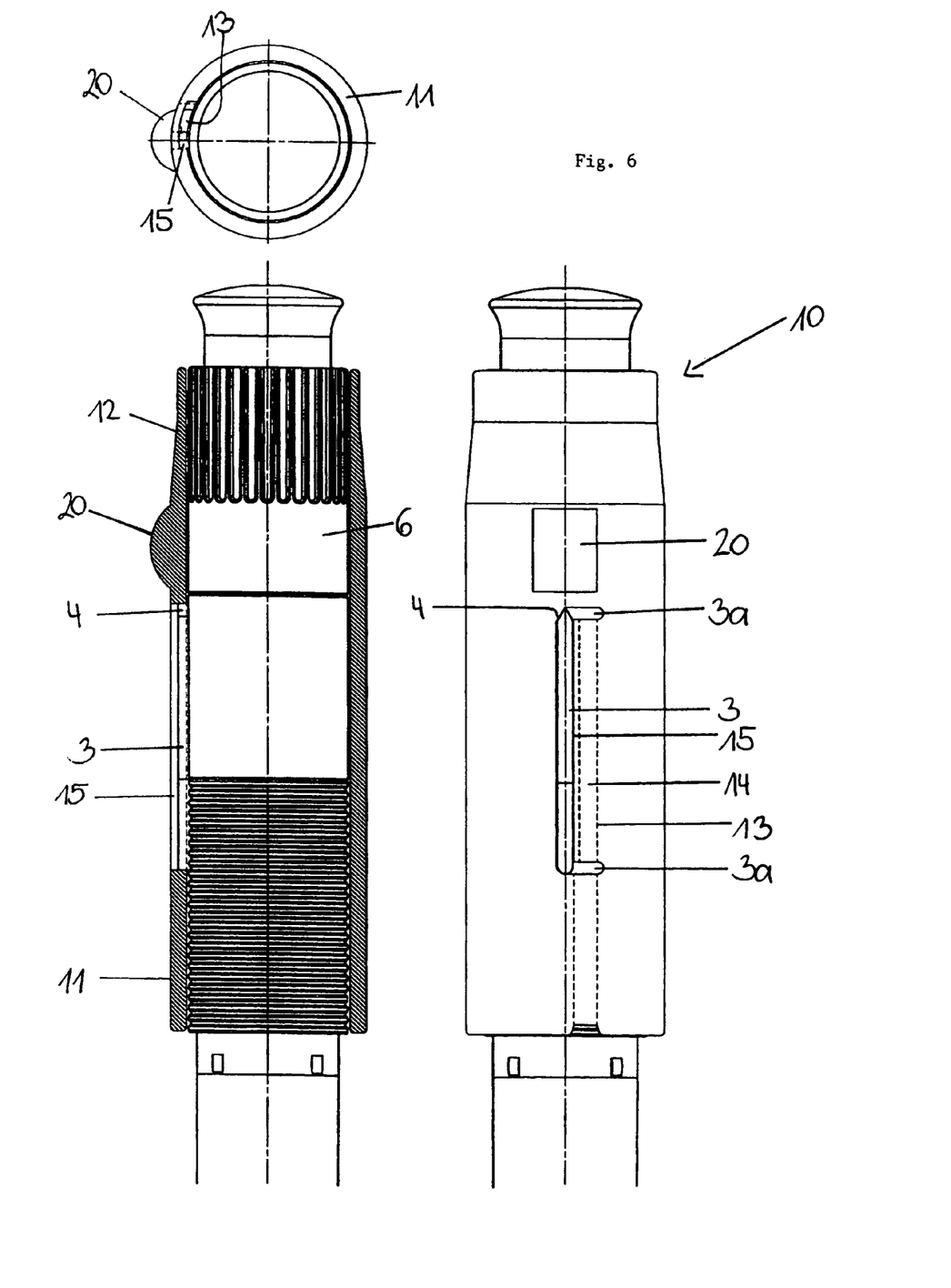
FIG. 6 depicts the injection apparatus comprising a plug-on body as set forth in a second exemplary embodiment.

The second exemplary embodiment of a reading aid and adjustment block, shown in FIG. 6, only differs from the first exemplary embodiment with respect to the latching connection. The latching elements 3a and 18 of the second exemplary embodiment are larger than those of the first exemplary embodiment. This results in a more stable latching connection, which requires a larger force to be employed to release it.

Figure 7:
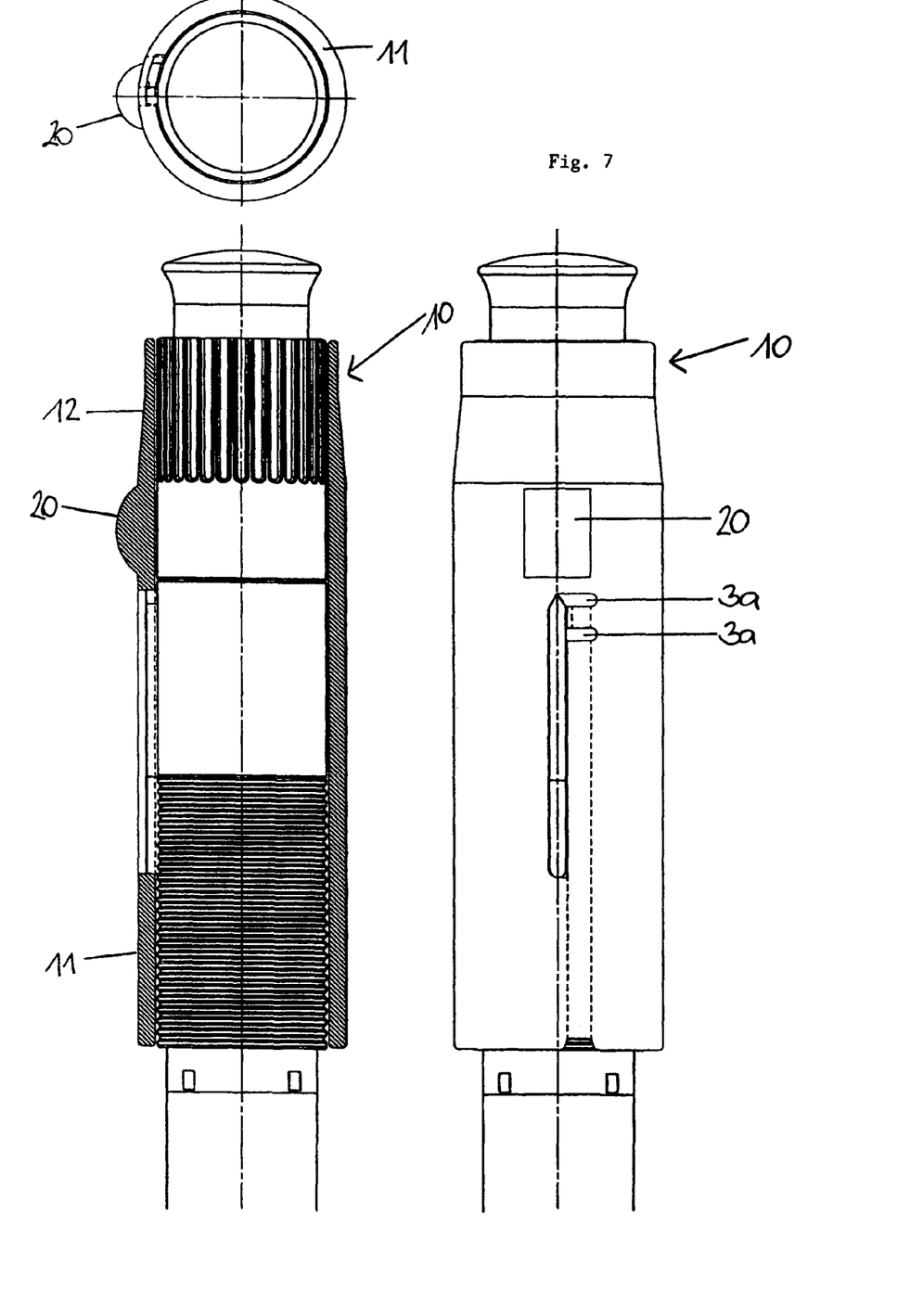
FIG. 7 depicts the injection apparatus comprising a plug-on body as set forth in a third exemplary embodiment.

The third exemplary embodiment shown in FIG. 7 corresponds to the second exemplary embodiment, the position of the latching elements 3a and 18 merely being varied in the third exemplary embodiment as compared to the second exemplary embodiment. By varying the axial gap between the latching elements 18 on the one hand and between the latching elements 3a on the other, the spring forces acting for the latching connection can be varied.

Figure 8:
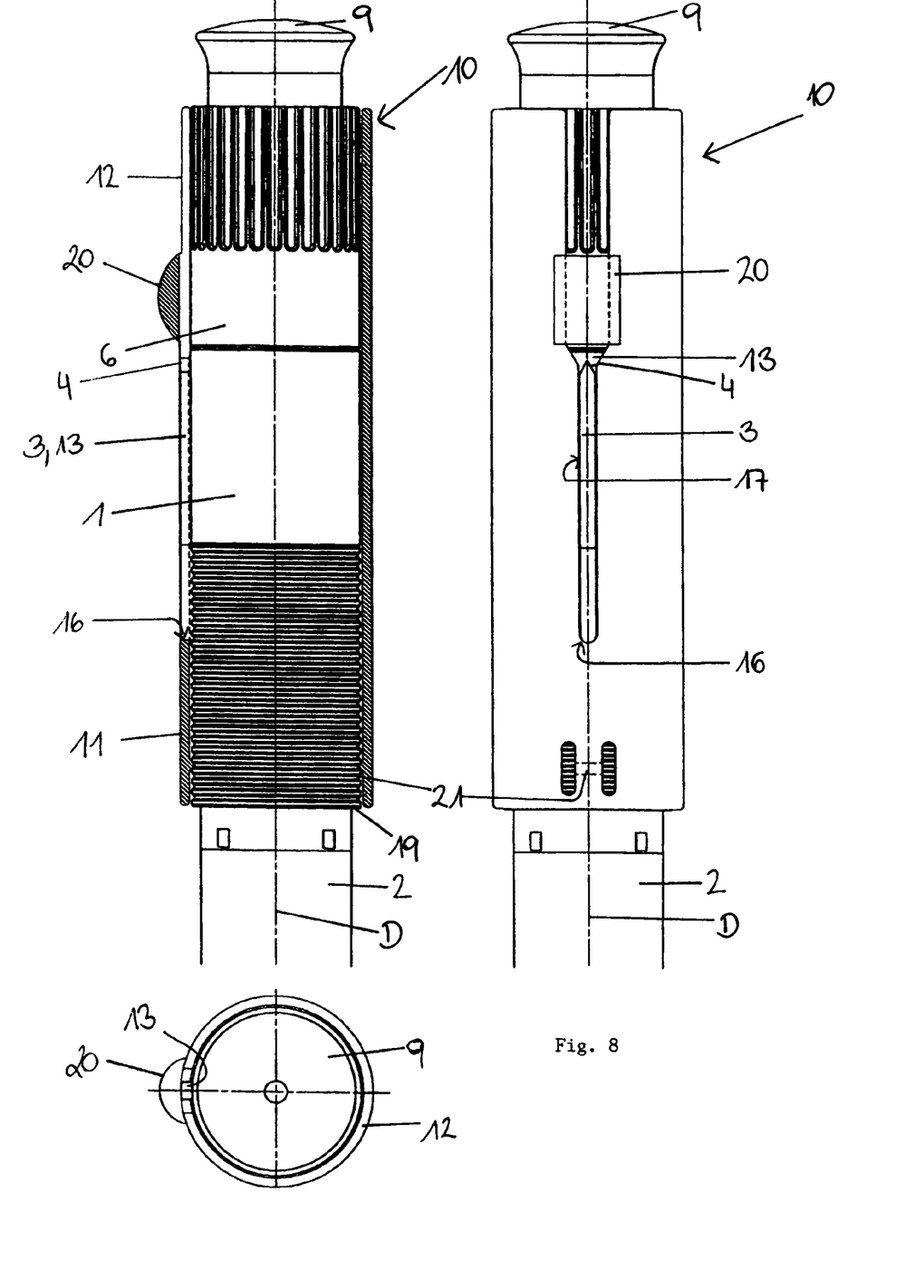
FIG. 8 depicts the injection apparatus comprising a plug-on body as set forth in a fourth exemplary embodiment.

FIG. 8 shows an injection apparatus/plug-on body combination as set forth in a fourth exemplary embodiment. The plug-on body 10 is again formed as a sleeve body. The functions of the plug-on body 10, namely fixing to the casing and preventing the dosing movement of the dosing element 6, are the same as in the plug-on bodies 10 of the exemplary embodiments already described.

The plug-on body 10 of the fourth exemplary embodiment, however, is not slid on via the activating element 9 but rather via the front end of the injection apparatus. In order to enable it to be slid on from the front, the recess 13 extends in the longitudinal direction of the plug-on body 10 as far as the rear facing side of the plug-on body 10. In order to enable a particularly good view of the marking arrow 4, the recess 13 is formed from its rear end up to its front end as a breach which is covered only by the reading-glass 20 arranged above it. The recess 13 forms a rotational stopper 17 acting in both directions and a shifting stopper 16 acting in a sliding direction, namely the sliding-on direction. Inadvertently retracting the plug-on body 10 to the front end of the injection apparatus is prevented by a latching connection.

The latching connection is established in this exemplary embodiment with the aid of the ribbing 19 provided on the guiding part 1. A latching element 21 is formed on the plug-on body 10, between two closely spaced breaches adjacent to each other in the circumferential direction, near a front end of the first plug-on body section 11. The surface area of the plug-on body between the two breaches is swelled radially inwards and forms an elastically flexible latching element 21 due to the two breaches. In the exemplary embodiment, two such latching elements 21 are formed diametrically opposite each other in the first plug-on body section 11. They engage with the circumferential grooves of the ribbing 19 of the guiding part 1, wherein the engagement can however be released due to the spring elasticity of the latching elements 21, by exerting a sufficient shifting force in the direction of the front end of the injection apparatus.

Figure 9:
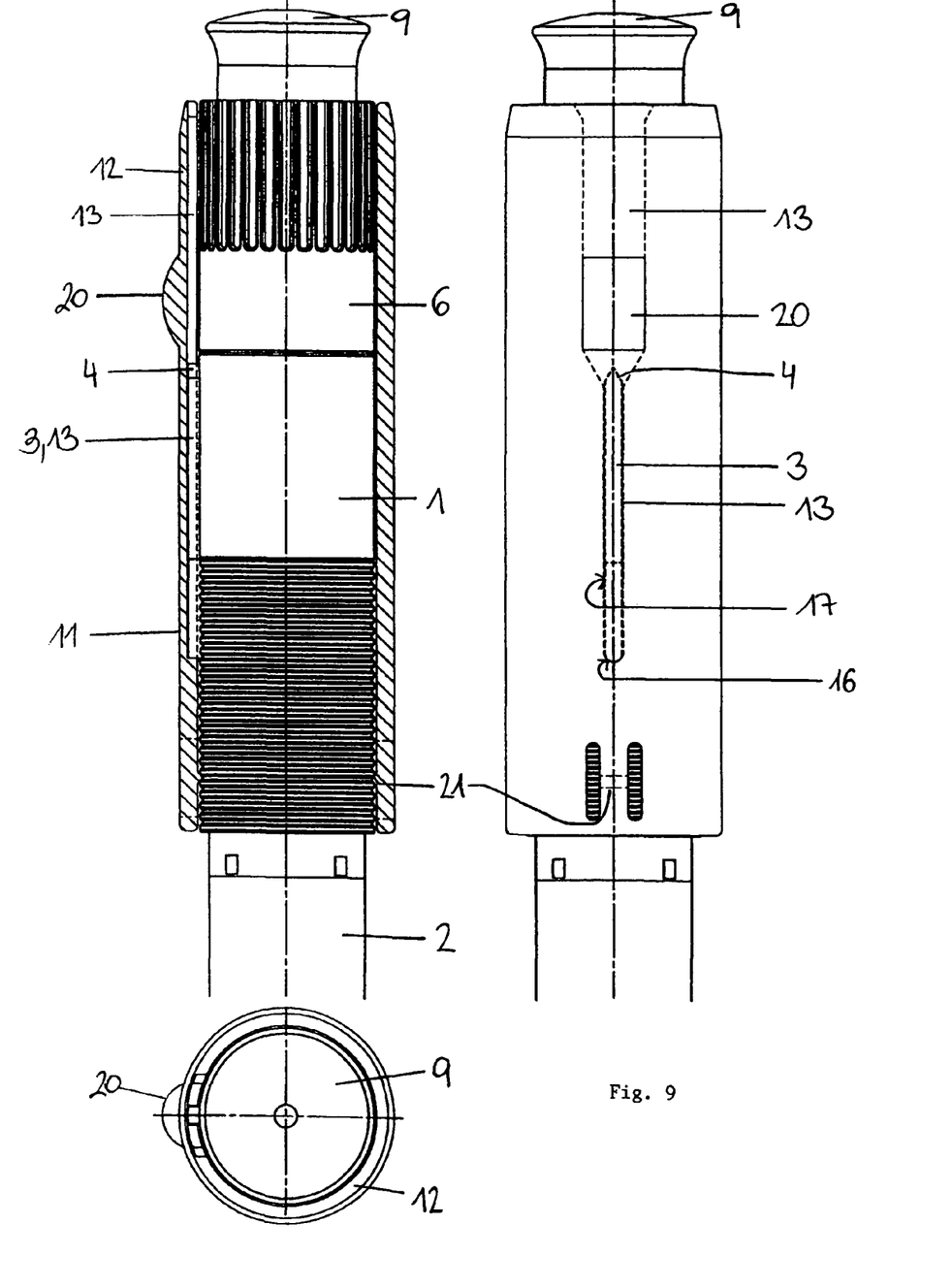
FIG. 9 depicts the injection apparatus comprising a plug-on body as set forth in a fifth exemplary embodiment.

FIG. 9 shows a reading aid and adjustment block as set forth in a fifth exemplary embodiment. The plug-on body 10 of this exemplary embodiment is substantially identical to the plug-on body 10 of the exemplary embodiment in FIG. 8. Unlike the exemplary embodiment in FIG. 8, however, the recess 13 is not formed as a breach but rather as a cavity on the inner surface area of the plug-on body 10. In order to form a defined rotational stopper 17, the wall thickness of the plug-on body 10 is correspondingly greater than in the preceding exemplary embodiment.

Figure 10:
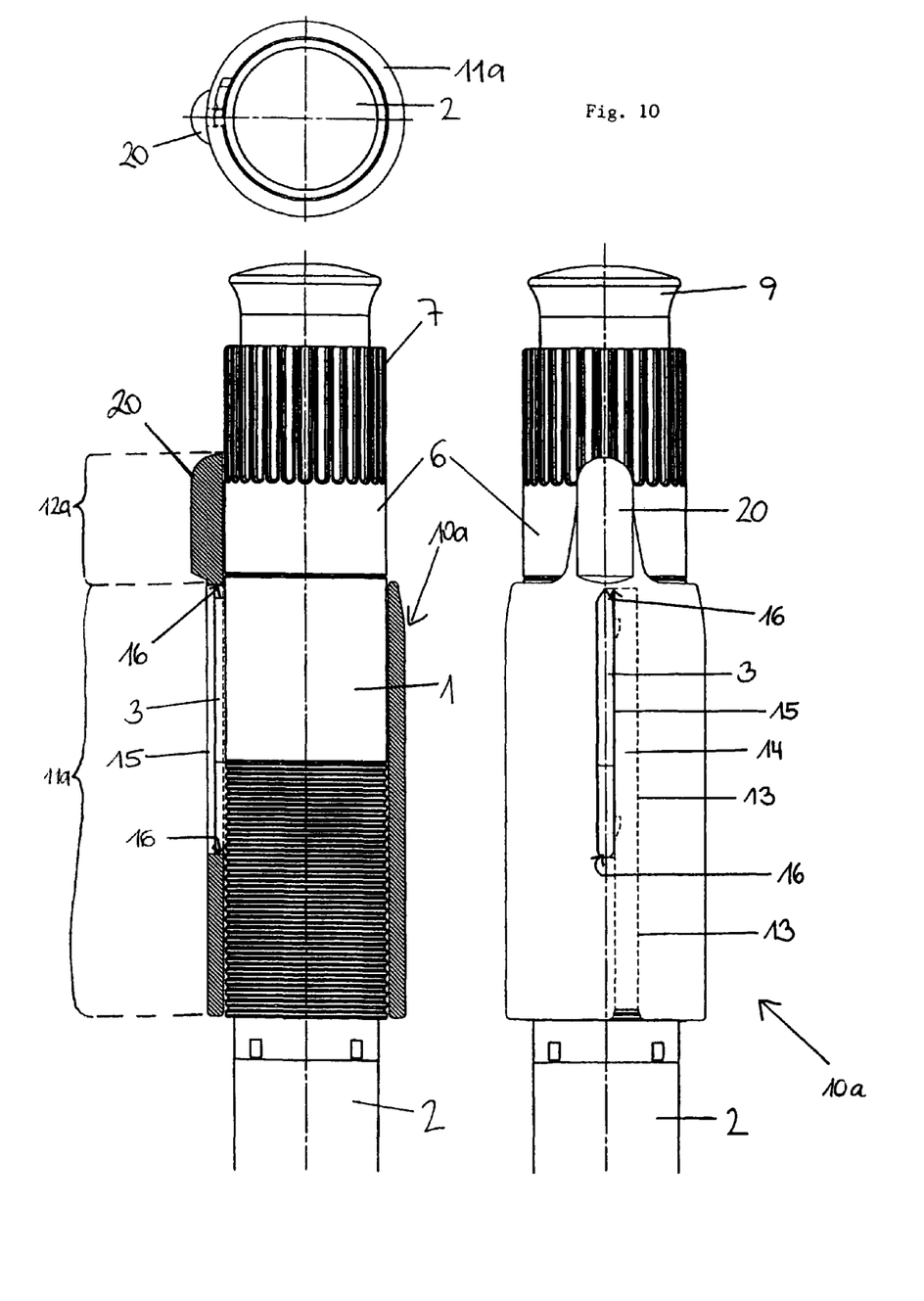
FIG. 10 depicts the injection apparatus comprising a reading aid formed by a plug-on body.

FIG. 10 shows a reading aid formed by a plug-on body 10a which is derived from the plug-on body 10 of the first exemplary embodiment but does not perform a blocking function. The plug-on body 10a generally corresponds to the plug-on body 10 of the first exemplary embodiment in its first section 11, such that in this respect reference may be made to the embodiment in the first exemplary embodiment. The second plug-on body section 12a, however, forms only the reading-glass 20 of the first exemplary embodiment and in this respect is achieved by reducing the second plug-on body section 12 of the first exemplary embodiment to the magnifying function, and also geometrically as a reduction to the reading-glass 20 which axially extends the first plug-on body section 11 like a tongue. The plug-on body 10a shows that the idea of the plug-on body which may be fastened to the casing of an injection apparatus, secured against shifting and rotating, can be used flexibly to fulfill additional functions employed in the sense of the invention to increase dosing reliability.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering device assembly comprising:
   a) an administering device having an outer casing, a rotating dosing mechanism for selecting a dose amount to be administered, an activating means for initiating administration of the injection, a dose delivery end, and a protrusion formed on the surface of the outer casing arranged distal to the dose delivery end;
   b) a first plug-on body section to be positioned on the outer casing of the device distal to the injection delivery end, said first plug-on body having an elongated groove extending along a longitudinal axis, wherein the elongated groove has a narrow portion for sliding accommodation of the protrusion formed on the surface of the outer casing of the device and a widened portion for accommodating the protrusion to lock the plug-on body to prevent axial and rotational movement of the plug-on body in relation to the outer casing of the device; and
   c) a second plug-on body section fixedly attached to the first plug-on-body section and positioned proximal to the activating means of the device and distal to the injection delivery end, wherein the second plug-on body section extends over the rotating dosing mechanism of the device, thereby preventing adjustment of the rotating dosing mechanism of the device, and wherein said second plug-on body section provides an optics system for reading a dosage scale of the rotating dosing mechanism of the device.

2. The plug-on body as set forth in claim 1, wherein the optics system provided by the second plug-on body section is a magnifying optics system.

3. The plug-on body as set forth in claim 1, wherein the plug-on body is transparent in at least a local area, the transparent area being arranged as a reading-glass for forming the optics system, such that once the plug-on body has been fixed, the dosage scale of the device can be read through said reading-glass.

4. The plug-on body as set forth in claim 1, wherein the second plug-on body section is formed by a shell body.

5. The plug-on body as set forth in claim 4, wherein said shell body is a sleeve body.

6. The plug-on body as set forth in claim 1, wherein the first plug-on body section is formed by a shell body provided with a recess that forms the elongated groove.

7. The plug-on body as set forth in claim 6, wherein the recess is a blind recess.

8. The plug-on body as set forth in claim 6, wherein the walls of a widened portion of the recess substantially perpendicular to the longitudinal axis of the device prevent movement of the plug-on body with respect to the outer casing of the device along the longitudinal axis of the device.

9. The plug-on body as set forth in claim 8, wherein a wall of the recess substantially parallel to the longitudinal axis of the device prevents rotational movement of the plug-on body with respect to the outer casing of the device around the longitudinal axis of the device.

10. The plug-on body as set forth in claim 6, wherein the first plug-on body section is provided with at least one latching element for establishing a latching connection with the outer casing of the device.

11. The plug-on body as set forth in claim 10, wherein said at least one latching element is formed in the recess.

12. A device for administering a settable dosage of an injectable product, said device comprising:
   a) a casing;
   b) a reservoir, formed or accommodated by the casing, from which a product dosage is administered;
   c) a delivering means for delivering the product dosage to be administered from said reservoir;
   d) an activating means, connected to the casing, with which the delivering means can be activated;
   e) a dosage mechanism for selecting a dose amount to be administered;
   f) a protrusion formed on the surface of the casing proximal to the dosage mechanism;
   g) a dose delivery end arranged distal to the protrusion; and
   h) a plug-on body which is arranged distal to the dose delivery end and forms an optics system for reading a dosage scale of the device when the plug-on body is connected to the casing, the plug-on body having an elongated groove extending along a longitudinal axis of the device, wherein the elongated groove has a narrow portion for accommodating the protrusion formed on the surface of the outer casing of the device and a widened portion for accommodating the protrusion to lock the plug-on body to prevent axial and rotational movement of the plug-on body in relation to the casing of the device, wherein when the plug-on body is locked, said plug-on body is arranged over the dosage mechanism thereby preventing its adjustment.

13. The device as set forth in claim 12, wherein the plug-on body comprises:

a) a first plug-on body section to be positioned on the outer casing of the device and having the elongated groove extending the length of the first plug-on body section along the longitudinal axis of the device; and b) a second plug-on body section fixedly attached to the first plug-on-body section and positioned proximal to the activating means of the device, wherein the second plug-on body section extends over the rotating dosing means of the device, thereby preventing adjustment of the rotating dosing means of the device.

14. The as set forth in claim 12, wherein the plug-on body comprises a first plug-on body section formed by a shell body provided with a recess and which forms at least one of a shifting stopper and a rotational stopper, wherein the recess is formed in the shell body, and wherein the protrusion radially projects from an outer surface area of the casing and engages, when it is connected, with the recess and presses against at least one of the shifting stopper and the rotational stopper.

15. The device as set forth in claim 14, wherein said protrusion is tapered towards the rotating dosing means and the activating means to form a marking arrow for a dosage scale of the dosing and activating means.

16. The device as set forth in claim 12, wherein the plug-on body forms a latching connection with the casing.

* * * * *